(12) United States Patent
Voegel et al.

(10) Patent No.: US 12,083,328 B2
(45) Date of Patent: Sep. 10, 2024

(54) DISPENSING OUTLET, DISPENSING SYSTEM, METHOD OF USING A DISPENSING SYSTEM, INJECTION MOLD AND METHOD OF PRODUCING A DISPENSING OUTLET

(71) Applicant: Sulzer Mixpac AG, Haag (CH)

(72) Inventors: Andreas Voegel, Wolfurt (AT); Christian Wieland, Malans (CH)

(73) Assignee: MEDMIX SWITZERLAND AG, Haag (CH)

( * ) Notice: Subject to any disclaimer, the term of this patent is extended or adjusted under 35 U.S.C. 154(b) by 551 days.

(21) Appl. No.: 17/276,551

(22) PCT Filed: Sep. 20, 2019

(86) PCT No.: PCT/EP2019/075293
§ 371 (c)(1),
(2) Date: Mar. 16, 2021

(87) PCT Pub. No.: WO2020/064532
PCT Pub. Date: Apr. 2, 2020

(65) Prior Publication Data
US 2022/0031963 A1 Feb. 3, 2022

(30) Foreign Application Priority Data
Sep. 26, 2018 (EP) ..................... 18196737
Mar. 7, 2019 (EP) ..................... 19161419

(51) Int. Cl.
*A61M 5/32* (2006.01)
*A61C 5/64* (2017.01)
(Continued)

(52) U.S. Cl.
CPC ............. *A61M 5/3294* (2013.01); *A61C 5/64* (2017.02); *A61C 9/0026* (2013.01);
(Continued)

(58) Field of Classification Search
CPC .............. A61M 5/3294; A61M 5/3129; A61M 2207/10; A61M 2207/00; A61M 5/32;
(Continued)

(56) References Cited

U.S. PATENT DOCUMENTS 2,750,068 A * 6/1956 Platt, Jr. ................. B65D 47/10
220/265
2,761,598 A * 9/1956 Darlington, Jr. ....... B65D 47/12
222/541.6
(Continued)

FOREIGN PATENT DOCUMENTS

CN 101035581 A * 9/2007 .......... A61M 5/5013
CN 201085658 Y 7/2008
(Continued)

OTHER PUBLICATIONS

International Search Report and Written Opinion issued Oct. 24, 2019 in corresponding International Patent Application No. PCT/EP2019/075293, filed Sep. 20, 2019.
(Continued)

*Primary Examiner* — Bob Zadeh
(74) *Attorney, Agent, or Firm* — GLOBAL IP COUNSELORS, LLP (57) ABSTRACT

A dispensing outlet includes a housing with a first end of the housing having a first outlet and a second end of the housing having a mixing or reception space. The mixing or reception space is configured to receive a further component, and a pre-determined breaking point is formed between the first outlet and the mixing or reception space.

29 Claims, 7 Drawing Sheets

(51) Int. Cl.
- *A61C 9/00* (2006.01)
- *A61M 5/31* (2006.01)
- *B29C 45/26* (2006.01)
- *B29L 31/00* (2006.01)

(52) U.S. Cl.
CPC ........... *A61M 5/3129* (2013.01); *B29C 45/26* (2013.01); *A61M 2207/10* (2013.01); *B29L 2031/7544* (2013.01)

(58) Field of Classification Search
CPC ......... A61M 5/1782; A61M 5/24; A61C 5/64; A61C 9/0026; A61C 5/62; B29C 45/26; B29L 2031/7544; B29L 2031/7548
See application file for complete search history.

(56) References Cited

U.S. PATENT DOCUMENTS

| | | | |
|---|---|---|---|
| 3,964,643 A * | 6/1976 | Morane | B65D 81/3222 222/541.6 |
| 4,012,822 A * | 3/1977 | Vrolyk | B29C 73/00 29/402.09 |
| 4,993,941 A | 2/1991 | Maita et al. | |
| 4,995,540 A | 2/1991 | Colin et al. | |
| 5,413,253 A * | 5/1995 | Simmen | B05C 17/00553 222/137 |
| 5,722,829 A * | 3/1998 | Wilcox | B05C 17/00506 222/137 |
| 6,135,771 A * | 10/2000 | Dragan | A61C 5/62 433/90 |
| 6,386,872 B1 | 5/2002 | Mukasa et al. | |
| 6,413,087 B1 | 7/2002 | Petrich et al. | |
| 6,488,991 B1 * | 12/2002 | Hunter | B05D 1/34 427/427.3 |
| 6,572,031 B2 | 6/2003 | Hunter et al. | |
| 6,672,519 B2 | 1/2004 | Hunter et al. | |
| 6,802,822 B1 | 10/2004 | Dodge | |
| 6,884,232 B1 | 4/2005 | Hagmann et al. | |
| 7,699,609 B2 | 4/2010 | Lawter et al. | |
| 8,770,450 B2 * | 7/2014 | Giraud | B65D 5/746 222/541.9 |
| 8,828,039 B2 | 9/2014 | Butz et al. | |
| 9,549,753 B2 | 1/2017 | Gordon | |
| 10,034,974 B2 | 7/2018 | MacLaughlan et al. | |
| 2007/0164047 A1 | 7/2007 | Reidt et al. | |
| 2007/0187434 A1 * | 8/2007 | Schrafel | B05B 7/0408 222/129 |
| 2011/0189630 A1 | 8/2011 | Koubi | |
| 2011/0273956 A1 | 11/2011 | Habibi-Naini et al. | |
| 2013/0158560 A1 * | 6/2013 | Gleason | A61B 17/8816 606/94 |
| 2015/0342715 A1 | 12/2015 | Hartman et al. | |
| 2017/0049532 A1 | 2/2017 | Koubi | |
| 2018/0221912 A1 * | 8/2018 | Haynes | B05C 17/00516 |
| 2019/0008611 A1 | 1/2019 | Müller | |

FOREIGN PATENT DOCUMENTS

| | | | |
|---|---|---|---|
| CN | 102098962 B | 3/2015 | |
| DE | 3882424 T2 | 11/1993 | |
| DE | 9319325 U1 | 2/1994 | |
| DE | 10005105 A1 * | 8/2001 | ............... B05B 9/01 |
| DE | 10 2016 001 429 A1 | 10/2016 | |
| DE | 102016122041 A1 * | 5/2018 | |
| DK | 2315553 T3 | 6/2015 | |
| EP | 2 315 553 B1 | 3/2015 | |
| EP | 2 574 572 B1 | 8/2015 | |
| ES | 2540464 T3 | 7/2015 | |
| FR | 2560050 A2 | 8/1985 | |
| GB | 2512123 A * | 9/2014 | ............. B05B 1/00 |
| JP | 2000041486 * | 2/2000 | |
| JP | 2000041486 A * | 2/2000 | |
| JP | 6494541 B2 | 4/2019 | |
| KR | 101528263 B1 | 6/2015 | |
| WO | WO-0244045 A1 * | 6/2002 | ............. B65D 35/06 |

OTHER PUBLICATIONS

Extended European Search Report issued Nov. 15, 2018 in corresponding European Patent Application No. 18196737.3, filed Sep. 26, 2018.

Chinese Search Report issued Nov. 21, 2022 in corresponding Chinese Application No. 201980062931.5.

Second Office Action issued Nov. 29, 2022 in corresponding Chinese Application No. 201980062931.5.

* cited by examiner

DISPENSING OUTLET, DISPENSING SYSTEM, METHOD OF USING A DISPENSING SYSTEM, INJECTION MOLD AND METHOD OF PRODUCING A DISPENSING OUTLET

CROSS-REFERENCE TO RELATED APPLICATIONS

This application is a U.S. National Stage application of International Application No. PCT/EP2019/075293, filed Sep. 20, 2019, which claims priority to European Patent Application No. 18196737.3, filed Sep. 26, 2018 and European Patent Application No. 19161419.7, filed Mar. 7, 2019, the contents of each of which are hereby incorporated herein by reference.

BACKGROUND

Field of the Invention

The present invention relates to a dispensing outlet comprising a housing with a first end of the housing having a first outlet and a second end of the housing having a mixing or reception space, the mixing or reception space configured to receive a further component, a pre-determined breaking point formed between the first outlet and the mixing or reception space. The present invention further relates to a dispensing system, to a method of using such a dispensing system, to an injection mold for the dispensing outlet and to a method of producing a dispensing outlet.

Background Information

Cartridges, in particular two component cartridges, are used for storage and subsequent dispensing of multi-component material. Such multi-component material is used in a plethora of fields of application ranging from industrial applications, such as the use of adhesives to bond structural components one to another, or as coatings for buildings or vehicles, to medical and dental applications, in particular as filling material, mold material or bleaching material. The multi-component material is, for example, a two-component adhesive comprising a filler material and a hardener. Multi-component cartridges are available with various ratios of filling, also known as mixing ratios, for example at mixing ratios of 1:1, 2:1, 4:1, 10:1 etc.

The multi-component materials stored in the cartridge can be mixed by activating the cartridge and then shaking its contents and guiding the mixed contents to an outlet to which a dispensing outlet is attached. Alternatively, the as yet unmixed respective material can be guided out of an outlet from the respective cartridge to a dynamic or static mixing element arranged within a mixer also known as a mixing tip, in which the material is mixed and then guided to an outlet from the mixing tip. In either case the outlet from the mixing tip or the outlet from the cartridge has one pre-defined outlet size. However, depending on the application different outlet sizes are desirable for the same multi-component material.

SUMMARY

In order to provide a user with a more versatile method of dispensing materials from the cartridge, tips can be attached to the mixing tip in order to reduce the diameter of the outlet opening from the mixing tip or the cartridge. The tips are generally also available in one size. Moreover, if the tips are not attached correctly at the mixing tip, then material can leak at the point of connection of the tips.

For this reason it is an object of the present invention to make available a more versatile dispensing outlet that can be used to dispense a variety of volumes of material via one and the same dispensing outlet on the avoidance of leaks. It is a further object of the present invention to make available a dispensing outlet that can be produced in a facile and cost-effective manner.

This object is satisfied by a dispensing outlet having the features disclosed herein.

In one embodiment, a dispensing outlet comprises a housing with a first end of the housing having a first outlet and a second end of the housing having a mixing or reception space, wherein the mixing or reception space is configured to receive a further component, wherein a pre-determined breaking point is formed between the first outlet and the mixing or reception space.

Forming the second end of the dispensing outlet such that it is configured to receive a further component, the dispensing outlet can either be configured to be placed directly at an outlet of a cartridge from which the ready to use material is dispensable directly from the cartridge. Alternatively the dispensing outlet can be configured to receive and store a mixing element therein that can be used to mix individual fluid flows of multi-component material to form the ready to use material that is then dispensable via the dispensing outlet.

On activating the pre-determined breaking point, the first outlet is separated from the dispensing outlet and beneficially sets free a second outlet that can have an outlet opening with a different size to that of the first outlet thereby making the dispensing outlet more versatile than prior art dispensing outlets.

Forming the dispensing outlet in one piece with first and second outlets ensures a facile method of manufacture and on use of the dispensing outlet avoids the presence of leaks on use of the first outlet.

Moreover, forming the pre-determined breaking point at a position that is remote from the mixing or reception space ensures the correct function of the mixing or reception space.

Further benefits and advantageous embodiments of the invention will become apparent from the description and from the accompanying drawings.

The dispensing outlet can hence comprise a second outlet that is arranged at the position of the pre-determined breaking point and that is set free on the separation of the first outlet from the mixing or reception space via the pre-determined breaking point. In this connection it should be noted that the term set free means that a new outlet is created or formed in the housing at the pre-determined breaking point by the act of breaking the housing at the pre-determined breaking point.

The second outlet can have an outlet opening with a larger diameter than that of the first outlet, in particular wherein the diameter of the outlet opening of the second outlet is 100 to 1000% larger, preferably 200 to 500% larger than the outlet opening of the first outlet. In this way one and the same dispensing outlet is made available and the user thereof can choose the required size of outlet for the desired application. If larger outlets are required, then the second outlet is set free via the pre-determined breaking point, whereas if a smaller outlet is required the first outlet can be used.

The dispensing outlet can be a mixer also known as mixing tip, such as a static mixer or a dynamic mixer, with the mixer comprising the mixing space, and the mixing space being configured to accommodate a mixing element and the pre-determined breaking point is formed between the first outlet and the mixing element. Thus, even though the mixer comprises two outlets one can ensure the same mixing quality of the multi-component material mixed with the mixing element of the mixer, as the mixing takes place at the mixing element and only then exits one of the outlets of the dispensing outlet.

By way of example, the mixing element can be a T mixer™, a helical type mixer a three way or four way mixer, or a dynamic mixing element.

A cannula can form the first outlet, with the cannula preferably being formed more flexible than the housing. Cannulas are advantageously used, e.g. in the dental field, in order to access regions that are not easily reached, such as a molar tooth, into which the multi-component material should be injected to form a filling. By forming the cannula more flexible than the housing, the cannula can be bent in use such that it can be reliably positioned at regions, e.g. the molar tooth, into which the multi-component material should be dispensed.

The difference in flexibility can be due to an inherent greater flexibility of the cannula material versus the material of the housing, such as due to a lower flexural Modulus (modulus of elasticity). Alternatively or additionally, the difference in flexibility can be due to the thinner wall dimensions and choice of, in particular metallic or plastic, material of the cannula in comparison to a material of the housing so that it has a lower bending strength or stiffness.

It should further be noted in this connection that it is preferable if the cannula is rotatably received in the housing, but in an axially fixed manner. It should further be noted that it is preferable if the cannula is configured such that it can be bent by up to 180 degrees relative to the longitudinal axis. An example of the functionality of such a cannula is the Colibri tip distributed by Sulzer Mixpac AG.

The cannula can be formed of a material different from that of the remainder of the housing, for example of metal. In this way the first outlet can be reliably formed in a cost-effective and reproducible manner.

Alternatively the cannula can be made from the same material as the housing. In this way the dispensing outlet can be formed in one injection mold in a single process which considerably reduces the cost of manufacture of the dispensing outlet.

A spacing between the pre-determined breaking point and an end of the mixing or reception space that is arranged closest to the pre-determined breaking point is less than an inner diameter of the housing surrounding the mixing or reception space. The materials that are dispensed using such dispensing outlets are comparatively expensive, reducing the spacings to such lengths, ensures that following the use of a dispensing outlet as little as possible of the multi-component material remains in the dispensing outlet as waste material.

The pre-determined breaking point can be formed in a wall of the housing, in this way the pre-determined breaking point can be formed as an integral part of the dispensing outlet.

The pre-determined breaking point can extend peripherally around the housing, in this way one can ensure the shape and size of the second outlet on removal of the first outlet from the dispensing outlet. By way of example the pre-determined breaking point can be formed by a groove that peripherally extends around the housing.

The housing can have a wall thickness which is larger than the wall thickness of the pre-determined breaking point. Forming the pre-determined breaking point of less material than the remainder of the housing enables the separation of the first outlet from the housing with a smaller force to be applied to remove the first outlet from the dispensing outlet.

The pre-determined breaking point is configured to withstand internal pressures of up to 5 bar, preferably 10 bar, more preferably of up to 15 bar, before leaking. In this way one can avoid leaks from arising in the region of the pre-determined breaking point on use of the first outlet.

A wall thickness of the housing at the position of the pre-determined breaking point can be selected in the range of 0.1 to 0.2 mm, in particular in the range of 0.12 to 0.18 mm and especially in the range of 0.14 to 0.16 mm. Such thicknesses have been found to ensure the formation of the second outlet at the position of the pre-determined breaking point, as well as a housing wall that is capable of being able to withstand internal pressure of up to 15 bar before springing a leak.

An internal diameter of the housing at the pre-determined breaking point can be smaller than an internal diameter of that part of the housing forming the mixing or reception space, can be larger than an internal diameter of that part of the housing forming the mixing or reception space or can be the same as an internal diameter of that part of the housing forming the mixing or reception space. In this way the internal diameter of the pre-determined breaking point can be manufactured in dependence on the possible application and the multi-component material.

The second end can comprise a coupling section via which the dispensing outlet can be coupled to a cartridge, with the coupling section preferably comprising an inlet section via which multi-component material can be guided to the mixer from outlets of the cartridge. In this way the dispensing outlet can be reliably and releasably coupled to a cartridge. This is particularly desirable with respect to dental or medical applications, where only a fraction of the multi-component material stored in the cartridge is used for a single application and is then stored for further applications at different later points in time, so that a releasable coupling of the dispensing outlet is highly desirable.

The pre-determined breaking point has one of a V-shaped cross-section, a V-shaped cross-section with a base, a U-shaped cross-section, and a L-shaped cross-section. Such cross-sections ensure the reliable function of the pre-determined breaking point and can be produced in a facile, reproducible, and cost-effective manner in an injection mold. It should be noted in this connection that the circumferentially extending groove forming the pre-determined breaking point can have the same cross-section perpendicular to its extend around the housing.

An opening angle of the V-shaped cross-section of the pre-determined breaking point can be selected in the range of 30 to 180°, especially in the range of 40 to 150° and especially in the range of 120 to 140° and in particular around 125 to 135°. Such opening angles enable the opening of the pre-determined breaking point in a reliable manner such that the second outlet is formed with the desired properties.

The housing can comprise a plastic, especially a thermoplastic; an elastomer, in particular silicone; and/or a thermosetting resin. Such materials ensure the reliable and cost-effective manufacture of the dispensing outlet.

An internal diameter of the housing can reduce in size between the pre-determined breaking point and the first outlet. In this way one ensures that the dispensing outlet has two outlets of varying size.

The dispensing outlet can further comprise a second pre-determined breaking point arranged between the pre-determined breaking point and the first outlet, the second pre-determined breaking point forming a third outlet that is arranged at the position of the second pre-determined breaking point and that is set free on separating the first outlet from the housing via the second pre-determined breaking point, with the third outlet optionally having an outlet opening having a larger diameter than that of the first outlet, but smaller than that of the second outlet.

In this way a dispensing outlet is made available that comprises three outlets and hence is even more versatile. In this connection it should be noted that a dispensing outlet with three or more pre-determined breaking points having four or more outlets may also be possible to generate a very versatile dispensing outlet.

According to a further aspect embodiments of the present invention relate to a dispensing system comprising one or more cartridges, each optionally filled with a material and a dispensing outlet in accordance with the teaching presented herein. Such a dispensing system can be used in a versatile manner.

The cartridge can be filled with an adhesive material or a coating material. The multi-component cartridge can thus be used in a plethora of fields of application ranging from industrial applications, such as the use of adhesives to bond structural components one to another, or as coatings for buildings or vehicles, to medical and dental applications, for example, to make dental molds.

The multi-component material stored in the cartridge can, for example, be a two-component adhesive comprising a filler material and a hardener.

According to a further aspect embodiments of the present invention relate to a method of using a dispensing system, the method comprising the step of setting free the second outlet by separating the first outlet from the dispensing outlet at the pre-determined breaking point.

In this connection it should be noted that the user of the dispensing system will preferably use the first outlet to dispense a portion of material from the cartridge in a precise manner over a small area, for example, for a precision impression, root canal filling, and cementation, and then after setting free the second outlet the same material will be dispensed over a larger or broader area in a coarser manner.

According to a further aspect embodiments of the present invention relate to an injection mold configured to form a dispensing outlet, the injection mold comprising an internal space, the internal space being configured to resemble an internal and external shape of the housing, with the internal space comprising an internal surface with one or more projections projecting from the internal surface reflecting the shape of the pre-determined breaking point or with one or more shutter elements being moveably formed in the mold with the shutter elements forming projections that project into the mold to form the pre-determined breaking point at the housing of the dispensing outlet.

The mold is thus adapted such that it provides recesses and undercuts matching the negative shape of the dispensing outlet. On use of such a mold dispensing outlets described herein can be beneficially made in a facile, reproducible and cost-effective manner.

According to a further aspect embodiments of the present invention relate to a method of making a dispensing outlet in an injection mold, the method comprising the step of:
injecting a molten mass of material into the internal space of the injection mold to integrally form the pre-determined breaking point at the housing of the dispensing outlet.

In this way dispensing outlets described herein can be beneficially made in a facile, reproducible and cost-effective manner.

It should be noted in this connection that the dispensing outlet described in the foregoing could also be formed in one of a 3D-printing process, a casting process and an extrusion process.

Regardless of the method of manufacture of the dispensing outlet the dispensing outlets can be subjected to a post treatment step, such as a mechanical or thermal post treatment step. By way of example, the pre-determined breaking point could be cut from the housing of the dispensing outlet e.g. in a mechanical process, for example, by using a saw, a milling tool or a lathe or in a thermal process e.g. through the use of a laser.

BRIEF DESCRIPTION OF DRAWINGS

The invention will be explained in more detail hereinafter with reference to the drawings.

DETAILED DESCRIPTION

In the following, the same reference numerals will be used for parts having the same or equivalent function. Any statements made having regard to the direction of a component are made relative to the position shown in the drawing and can naturally vary in the actual position of application.

Figure 1:
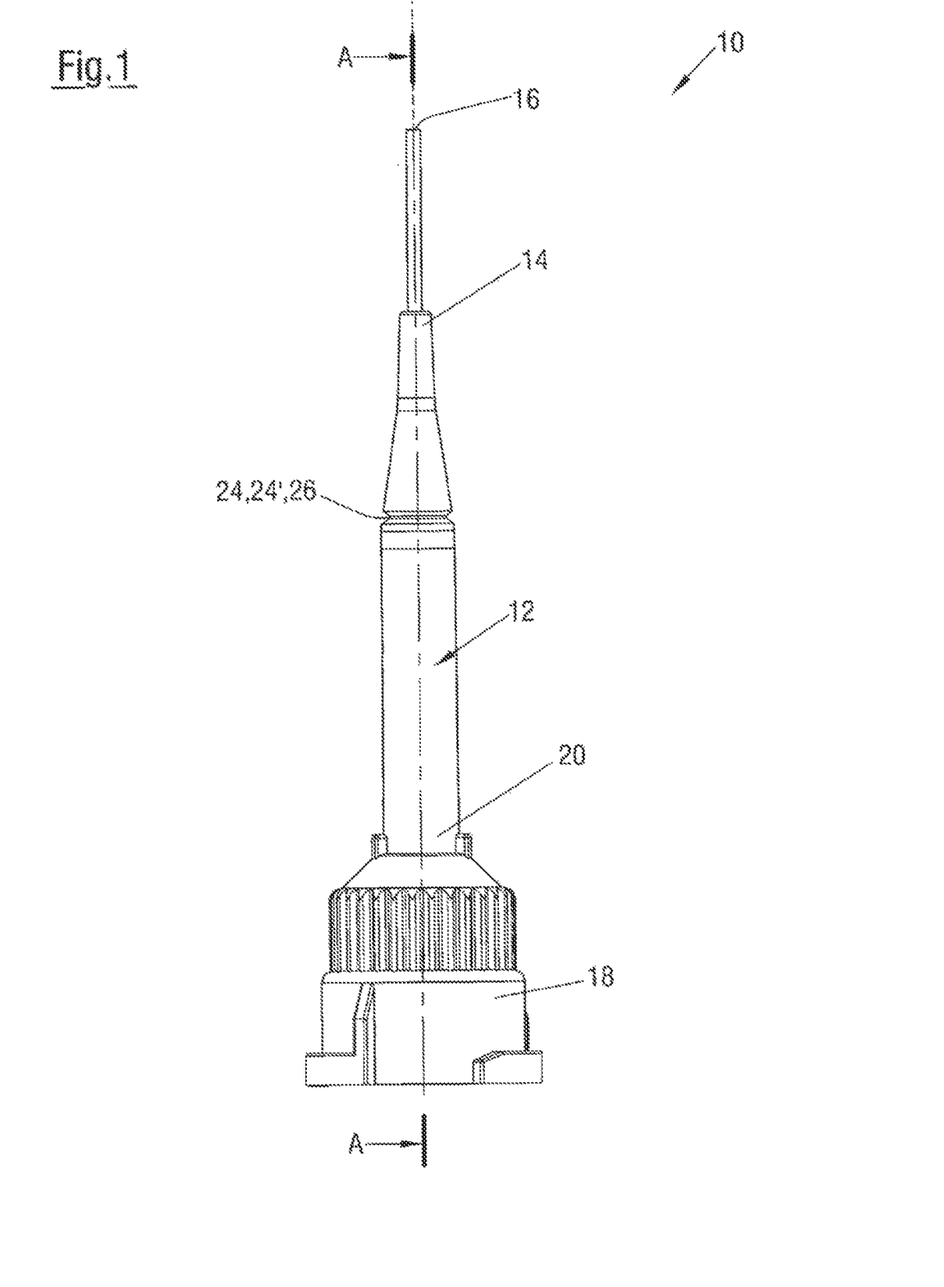
FIG. 1 is a side view of a first type of dispensing outlet.

FIG. 1 shows a perspective view of a first type of dispensing outlet 10. The dispensing outlet 10 comprises a housing 12 with a first end 14 of the housing 12 having a first outlet 16 and a second end 18 of the housing 12 having a mixing or reception space 20 formed therein. The first end 14 is oppositely disposed of the second end 18 along the longitudinal axis A of the dispensing outlet 10.

Figure 7:
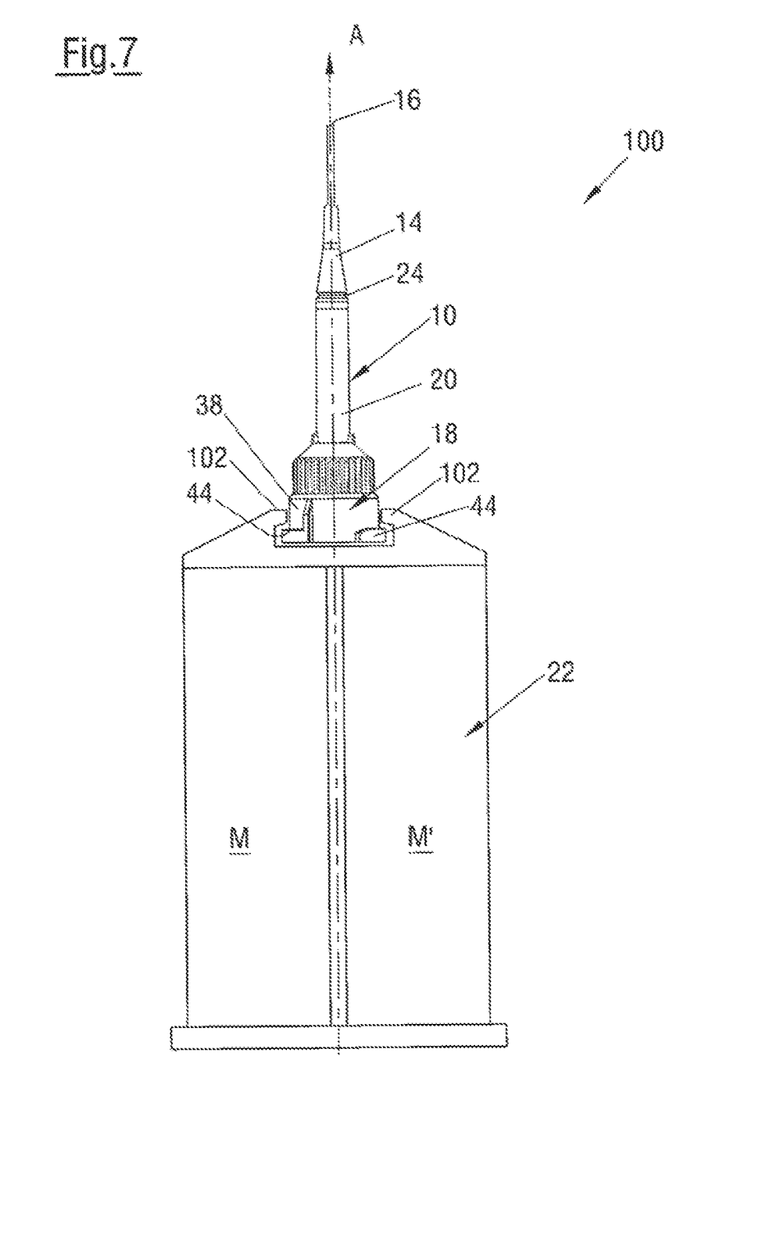
FIG. 7 is a schematic view of a dispensing system

The mixing or reception space 20 is configured to receive a further component, such as a cartridge 22, which is illustrated in FIG. 7. A pre-determined breaking point 24 is formed at the housing 12 between the first outlet 16 and the mixing or reception space 20.

The pre-determined breaking point 24 is formed in a wall 12' (see FIG. 2) of the housing 12 and peripherally extends around the housing 12 in the form of a groove 24'. The wall 12' of the housing 12 generally has a wall thickness which is larger than the wall thickness of the pre-determined breaking point 24. In this connection it should be noted that the pre-determined breaking point 24 can have a wall thickness selected at the thinnest point of the pre-determined breaking point 24 in the range of 5 to 60% of the wall thickness of the wall 12' of the housing 12 at the thickest point of the wall 12'.

It should further be noted that a wall thickness of the thinnest point of the pre-determined breaking point 24, i.e. a base of the groove 24', is selected such that the pre-determined breaking point 24 is configured to withstand internal pressures of up to 5 bar, preferably 10 bar, more preferably of up to 15 bar before leaking.

In this connection a simple bursting test can be performed, during which one end of the housing is blocked off and the pressure within the housing is increased up until the desired pressure is obtained. If the housing does not burst then the housing satisfies the above requirements. If the housing bursts then it does not satisfy the above requirements.

Figure 5:
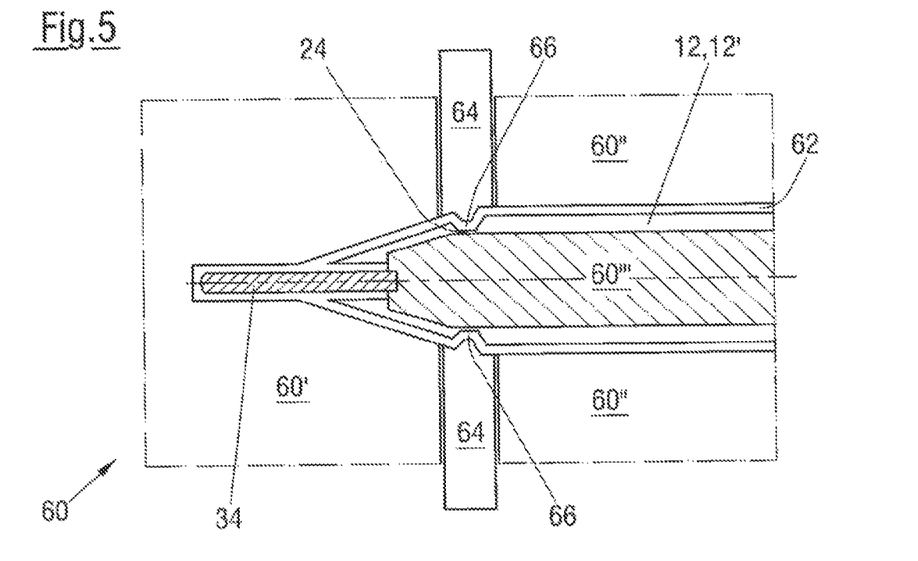
FIG. 5 is a schematic sectional view through a first type of injection mold for forming the dispensing outlet.
Figure 6:
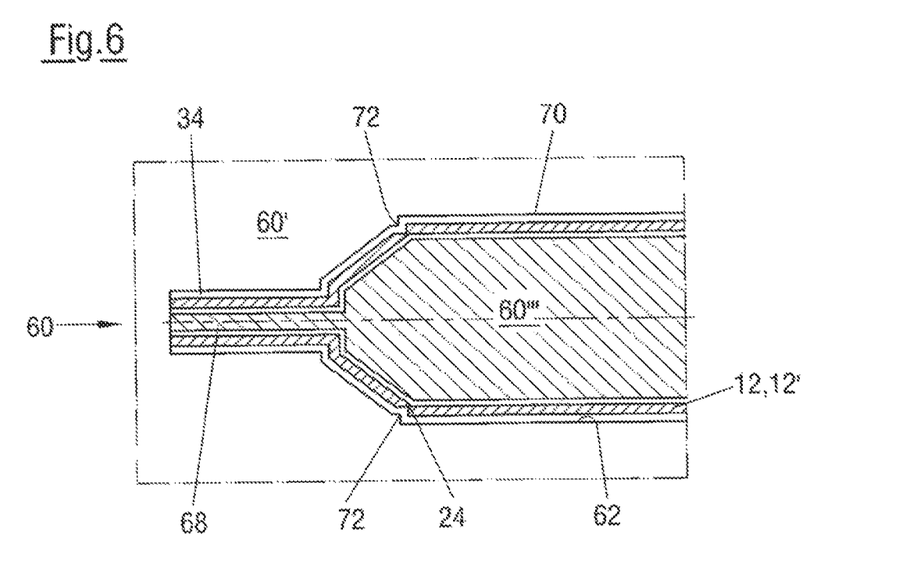
FIG. 6 is a schematic sectional view through a second type of injection mold for forming the dispensing outlet.

In the example of FIG. 1, the pre-determined breaking point 24, i.e. the groove 24' forming the pre-determined breaking point 24, has a V-shaped cross-section perpendicular to the longitudinal axis A, with a valley of the V facing towards the longitudinal axis A. Other types of cross-sections of the pre-determined breaking point 24 can be employed, such as a V-shaped cross-section with a base as shown in FIG. 5, a U-shaped cross-section, or a L-shaped cross-section as shown in FIG. 6.

The dispensing outlet 10 comprises a second outlet 26 that is arranged at the position of the pre-determined breaking point 24 and that is set free on separating the first outlet 16 from the mixing or reception space 20 via the pre-determined breaking point 20. The second outlet 26 has an outlet opening 28 (see FIG. 2) with a larger diameter than an outlet opening 30 of the first outlet 16 (also shown in FIG. 2).

Figure 2:
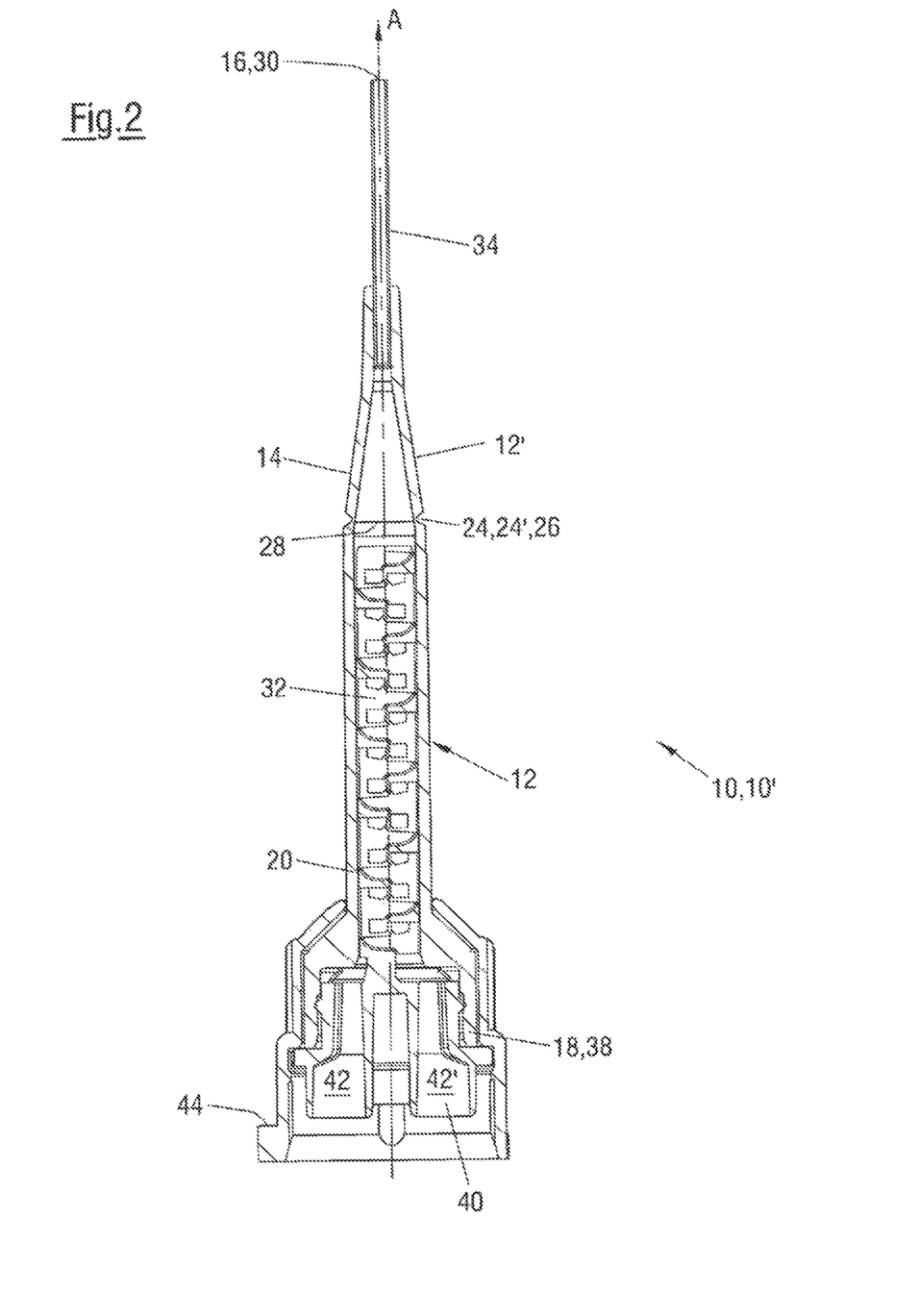
FIG. 2 is a sectional view through the first type of dispensing outlet of FIG. 1.

As shown in more detail in FIG. 2, the dispensing outlet 10 is a mixer 10', more specifically a static mixer 10', comprising the mixing space 20, with the mixing space 20 being configured to accommodate a mixing element 32. The pre-determined breaking point 24 is formed between the first outlet 16 and the mixing element 32.

The first outlet 16 is formed by a cannula 34. The cannula 34 is more flexible than the housing 12 such that it can be bent away from the longitudinal axis A in use of the dispensing outlet 10. Furthermore, the cannula 34 is received in the first end 14 such that it is axially fixed in position, i.e. it cannot be moved to and fro along the longitudinal axis A, but is rotatable about the longitudinal axis A.

The cannula 34 can be formed of a material different from that of the remainder of the housing 12, for example of metal. If a metal cannula 34 is selected then this has to be so thin walled that it can be bent while the housing 12 is not deformed.

Alternatively the cannula 34 can be formed from the same material as that of the housing 12. In this connection it should be noted that the housing 12 can be made from a plastic, especially a thermoplastic; an elastomer, in particular silicone; and/or a thermosetting resin.

An internal diameter of the housing 12 at the pre-determined breaking point 24, i.e. the diameter of the outlet opening 26, is smaller than an internal diameter of that part of the housing 12 forming the mixing or reception space 20, i.e. the space configured to receive the mixing element 32 in FIG. 2.

Alternatively the internal diameter of the housing 12 at the pre-determined breaking point 24 can be larger than an internal diameter of that part of the housing 12 forming the mixing or reception space or can be the same as an internal diameter of that part of the housing 12 forming the mixing or reception space 20.

The second end 18 comprises a coupling section 38 via which the dispensing outlet 10 can be coupled to the cartridge 22. The coupling section 38 comprises an inlet section 40 via which multi-component material M, M' (see FIG. 7) can be guided to the mixer 10' from outlets (not shown) of the cartridge 22. The inlet section 40 comprises two inlets 42, 42' via which the multi-component material M, M' can be guided from the respective outlet of the cartridge 22 to the mixing element 32.

The coupling section 38 further comprises a connecting part 44 comprising bayonet-like attachment means (or element) that are used to removeably attach the dispensing outlet 10 at the cartridge 22. This assembly is shown and discussed in more detail in connection with FIG. 7.

Other forms of connecting parts 44 can also be used as are well known to the person skilled in the art, for example, the cartridge 22 can have a threaded portion (not shown) and the dispensing outlet 10 can be removeably attached to the cartridge 22 via a nut-like element (also not shown).

As is also shown in FIG. 2 an internal diameter of the housing 12 reduces in size between the pre-determined breaking point 24 and the first outlet 16.

In this connection it should be noted that the internal diameter of the housing 12 reduces from a size of 100% at the pre-determined breaking point 24 to a size selected in the range of 1 to 30%, in particular 2 to 20 of the housing 12 at the first outlet 16.

Figure 3:
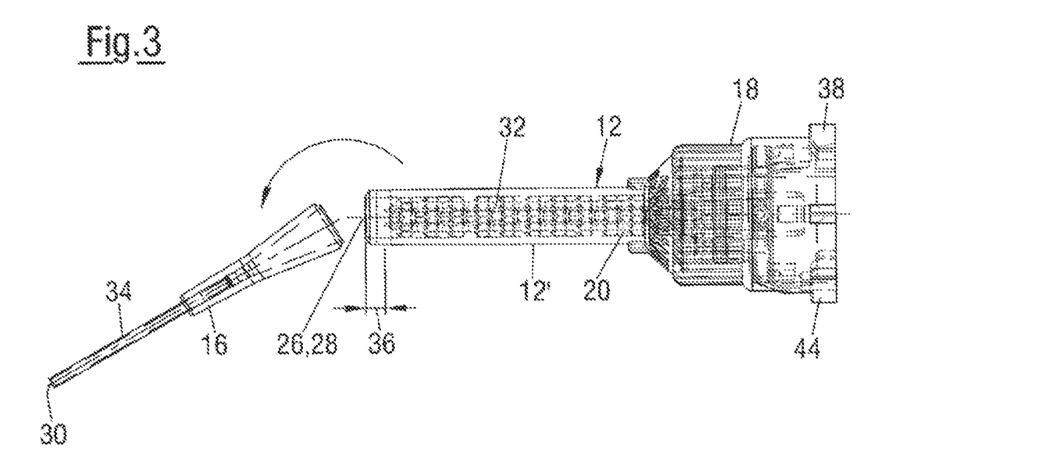
FIG. 3 is a sectional view of a second type of dispensing outlet similar to FIG. 1 in an activated state.

FIG. 3 shows a sectional view of a second type of dispensing outlet 10 similar to the one shown in FIGS. 1 and 2 in an activated state, i.e. a state in which the second outlet 26 is set free by separating the first outlet 16 from the housing 12 via the pre-determined breaking point 24.

The difference between the dispensing outlet 10 of FIGS. 1 & 2 and that shown in FIG. 3 is the different mixing element 32 used. In this connection, there is no restriction on the type of mixing elements 32 that can be used with the dispensing outlet 10 described herein.

By way of example, a T-mixer mixing element 32 as shown in FIG. 1 and as sold by Sulzer Mixpac AG can be used, as can a helical shaped mixing element 32 also sold by Sulzer Mixpac AG. Also further types of mixing elements 32 that are available on the market can be used in conjunction with the dispensing outlet 10.

A spacing 36 between the pre-determined breaking point 24 and an end of the static mixing element 32 is less than an outer diameter of the static mixing element 32 respectively of an inner diameter of the housing 12 surrounding the mixing or reception space 20. In the example shown the spacing 36 is 1.9 mm. In this connection it should be noted that the spacing 36 is typically selected such that it corresponds to 30 to 95% of the outer diameter of the static mixing element 10'.

Figure 4:
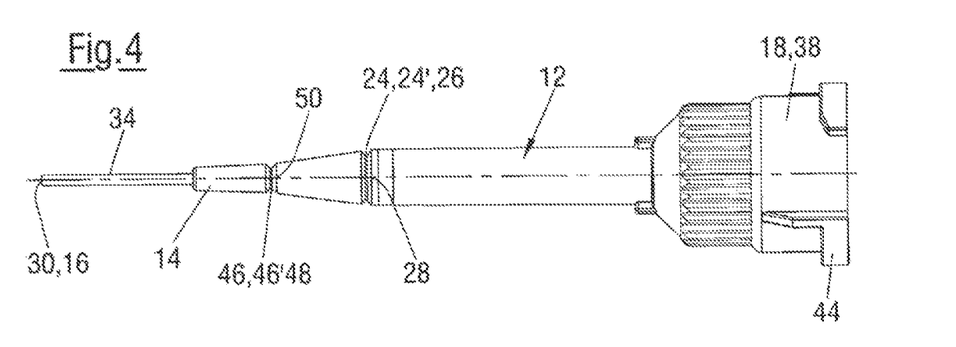
FIG. 4 is a side view of third type of dispensing outlet.

FIG. 4 shows a side view of a third type of dispensing outlet 10. The dispensing outlet 10 further comprises a second pre-determined breaking point 46 that is positioned between the pre-determined breaking point 24 and the first outlet 16.

The second pre-determined breaking point 46 forms a third outlet 48 that is arranged at the position of the second pre-determined breaking point 46 and that is set free on separating the first outlet 16 from the housing 12 via the second pre-determined breaking point 46. It should be noted in this connection that the second pre-determined breaking point 46 can be configured in an analogous way to the first pre-determined breaking point 24, i.e can also be formed as a peripherally extending groove 46'.

The third outlet 48 has an outlet opening 50 having a larger diameter than that of the first outlet 16, but smaller than that of the second outlet 26.

FIG. 5 shows a schematic sectional view of a first type of injection mold 60 for forming the dispensing outlet 10 as described herein. The injection mold has respective inputs for the components to be injected (not shown) and for any required vacuum apparatus (also not shown). In order to mold the dispensing outlet 10 inserts 60', 60", 60''' specific to the shape of the dispensing outlet 10 are also introduced into the injection mold 60.

The injection mold 60 comprises an internal space 62, the internal space is configured as a negative mold for the housing of the dispensing outlet 10, i.e. it is configured to resemble the internal and external shape of the housing 12. A shape of the internal space 62 is defined by the outer shape of the respective inserts 60', 60", 60''' and 68 (see FIG. 6) respectively used to form the desired dispensing outlet 10.

In order to form the pre-determined breaking point 24 shutter elements 64 are moveably arranged in the injection mold 60. The shutter elements 64 comprise projections that project into the internal space 62 and form a negative shape of the pre-determined breaking point 24, i.e. of the groove 24'. In the present example the pre-determined breaking point 24 to be formed has a V-shaped cross-section with a base 66. In the example of FIG. 5, the cannula 34 forms part of the mold 60 and the housing 12 is injection molded around the cannula 34.

FIG. 6 shows a further schematic sectional view through a second type of injection mold 60 for forming the dispensing outlet 10. The internal space 62 comprises an internal surface 70, with a projection 72 projecting from the internal surface 70 and into the injection mold 60. The projection 72 is shaped such that it reflects a negative shape of the pre-determined breaking point 24 that is to be formed in the injection mold 60. In the present instance a L-shaped pre-determined breaking point 24.

On using the respective injection mold 60, a molten form of the material forming the housing 12 and optionally that of the cannula 34 is injected into the internal space 62 of the injection mold 60 to integrally form the pre-determined breaking point 24 at the housing 12 of the dispensing outlet 10.

FIG. 7 shows a schematic side view of a dispensing system 100. The dispensing system 100 comprises a two-component cartridge 22, with each of the cartridges thereof being filled with respective material M, M' that is to be mixed by the mixing element 32 in the dispensing outlet 10.

The dispensing outlet 10 is attached to the cartridge 22 via the coupling section 38 and specifically via the connecting part 44 that cooperates with connecting members 102 present at the cartridge 22 and additionally through the interaction between the inlets 42, 42' into the coupling section 38 of the dispensing outlet 10 and the outlets from the cartridge 22.

Figure 8:
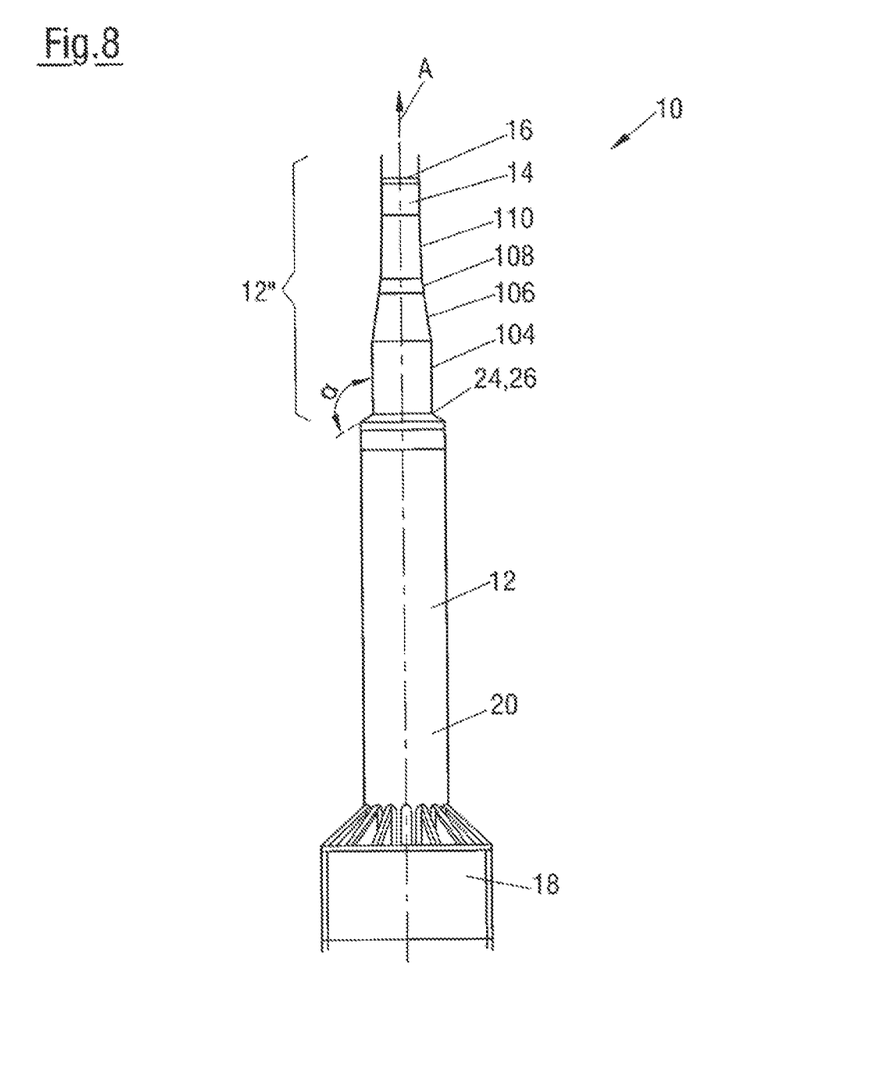
FIG. 8 is a side view of a fourth type of dispensing outlet.

FIG. 8 shows a side view of a fourth type of dispensing outlet 10. The pre-determined point 24 of this dispensing outlet 10 has a V-shaped cross-section. In contrast to the first type of dispensing outlet 10 shown in FIG. 1, the pre-determined breaking point is not formed as a groove 26. An opening angle a of the V-shaped cross-section of the pre-determined breaking point is selected as 130°.

In this connection it should be noted that generally speaking the opening angle a of the V-shaped cross-section of the pre-determined breaking point 24 can be selected in the range of 30 to 180°, especially in the range of 40 to 150° and especially in the range of 120 to 140° and in particular around 125 to 135°. These parameters also hold true for the first type of dispensing outlet 10.

The first outlet 16 is formed at the first end 14 of the dispensing outlet 10 also in the form of the cannula 34 (not shown in FIG. 8). The first outlet 16, i.e. the cannula is formed in a part of the housing 12 that has a reduced outer diameter in comparison to the outer diameter of the pre-determined breaking point.

The housing part 12" of the housing 12 housing the first outlet 16 between the pre-determined breaking point 24 and the first end 14 is formed by a first tapering part 104 that is arranged directly adjacent to a second tapering part 106. The second tapering part 106 is arranged between the first tapering part 104 and a third tapering part 108 that has a smaller outer diameter than the first tapering part 104. The end of the housing part 12" comprising the first end 14 is formed by a cylindrical part 110.

In this connection it should be noted that a maximum wall thickness of the first tapering part 104 can be selected in the range of 0.3 to 0.9, in particular 0.4 to 0.7 mm.

In this connection it should further be noted that the wall thickness of the wall 12' of the housing 12 at the thickest point of the wall 12' is selected in the range of 0.5 to 1 mm, in particular in the range of 0.6 to 0.9 mm.

It should further be noted that the wall thickness of the wall 12' of the housing 12 at the thickest point of the wall 12' can be selected larger than the maximum wall thickness of the first tapering part 104.

It should further be noted that a diameter of the outlet opening 28 of the second outlet 26 at the position 24" of the pre-determined breaking point 24 is selected in the range of 3 to 6 mm, in particular 3.5 to 4.5 mm.

The cannula 34 is typically arranged such that it is axially held in position at the first end 14, namely within the cylindrical part 110, i.e. such that it cannot move to and fro along the longitudinal axis A, but nevertheless such that it can be rotated about the longitudinal axis A.

Both the first, second and the third tapering parts 104, 106, 108 taper in the direction of the first end 14 such that the outer diameter of the housing part 12" reduces between the pre-determined breaking point 24 and the first outlet 16.

Figure 9:
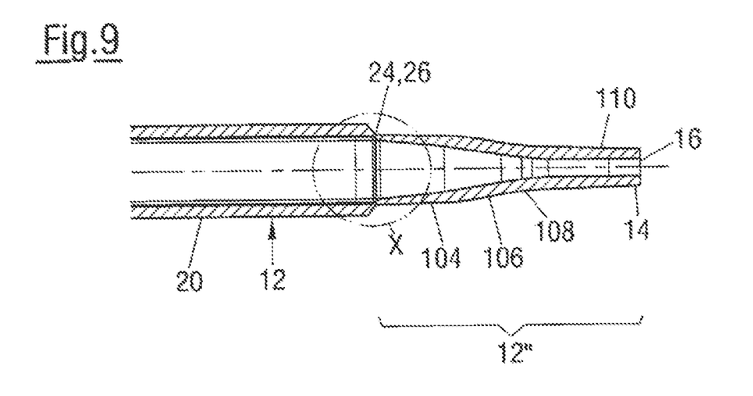
FIG. 9 is a sectional view through the fourth type of dispensing outlet.

FIG. 9 shows a sectional view through the fourth type of dispensing outlet 10. The angle of the tapers of the first, second and the third tapering parts 104, 106, 108 are different from one another, especially with the first tapering part 104 having a smaller taper than the second tapering part 106. The second tapering part 106 has a larger taper than the third tapering part 108.

Figure 10:
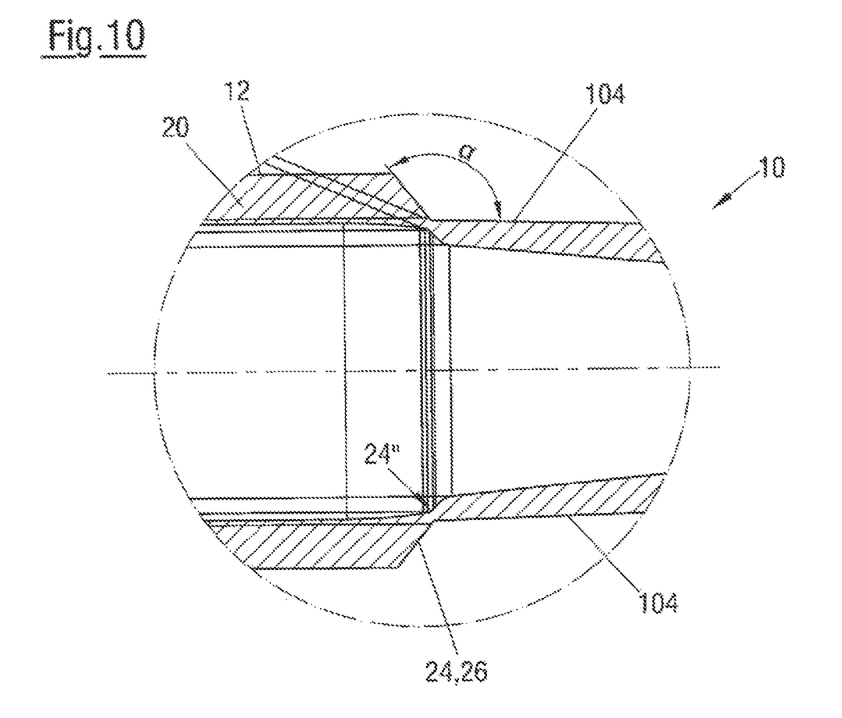
FIG. 10 is an enlarged view of section X of FIG. 9.

FIG. 10 shows an enlarged view of section X of FIG. 9. A wall thickness of the housing 12 at the position 24" of the pre-determined breaking point 24 is selected as 0.15 mm.

Generally speaking the wall thickness of the position 24" of the pre-determined breaking point 24 may be selected in the range of 0.1 to 0.2 mm, in particular in the range of 0.12 to 0.18 mm and especially in the range of 0.14 to 0.16 mm.

As can clearly be seen the wall thickness of the housing 12 is larger at either side of the pre-determined breaking point 24 in order to reliably form the second outlet 26 at the position 24" of the pre-determined breaking point 24. The housing wall 12 is namely formed such that its thickness reduces up to the position 24" of the pre-determined breaking point at either side of the pre-determined breaking point 24.

It should be noted in this connection that the cannula 34 can be arranged in the housing part 12" such that it is end opening into the dispensing outlet 10 is arranged solely within the cylindrical part 110. The cannula 34 can also be arranged such its end opening into the dispensing outlet 10 is arranged somewhere between the cylindrical part 110 and an end of the mixing element 32.

On using the dispensing system 100, the cartridge 22 and dispensing outlet 10 are typically inserted into a dispenser (not shown). The user of the dispensing system then decides which outlet size is required for the desired application. On choosing the desired application the user then proceeds to either use the first outlet 16 or to use either of the second and third outlets 26, 46 by separating the first outlet 16 from the housing 12 via the respective pre-determined breaking point 24, 46. The dispenser is then used to dispense the multi-component material M, M'. The multi-component material M, M' is then discharged from the dispensing system via the respective outlet 16, 26, 48.

The invention claimed is:

1. A dispensing outlet comprising:
   a housing and a pre-determined breaking point, the housing comprising a first housing part and a second housing part, the first housing part housing a first outlet between a first end of the housing and the pre-determined breaking point and the second housing part accommodating a mixing or reception space between a second end of the housing and the predetermined breaking point, the mixing or reception space configured to receive a mixing element, and the pre-determined breaking point being formed between the first outlet and the mixing or reception space by a tapering part of the first housing part tapering towards the first end and an outer wall of the second housing part such that the pre-determined breaking point has a V-shaped cross-section, and an opening angle of the V-shaped cross-section of the pre-determined breaking point is selected in the range of 120 to 140°.

2. The dispensing outlet in accordance with claim 1, wherein the dispensing outlet comprises a second outlet arranged at a position of the pre-determined breaking point and set free on separation of the first outlet from the mixing or reception space via the pre-determined breaking point.

3. The dispensing outlet in accordance with claim 2, wherein the first outlet has a first outlet opening and the second outlet has a second outlet opening, a diameter of the second outlet opening is larger than a diameter of the first outlet opening.

4. The dispensing outlet in accordance with claim 3, wherein the diameter of the second outlet opening is 100 to 1000% larger than the diameter of the first outlet opening.

5. The dispensing outlet in accordance with claim 3, wherein the diameter of the second outlet opening is 200 to 500% larger than the diameter of the first outlet opening.

6. A dispensing system comprising:
   one or more cartridges, each filled with a multi-component material; and
   a dispensing outlet in accordance with claim 2.

7. A method of using a dispensing system in accordance with claim 6, the method comprising:
   setting free the second outlet by separating the first outlet from the dispensing outlet at the pre-determined breaking point.

8. The dispensing outlet in accordance with claim 1, wherein the dispensing outlet is a mixer comprising the mixing space, with the mixing space being configured to accommodate the mixing element and the pre-determined breaking point being formed between the first outlet and the mixing element.

9. The dispensing outlet in accordance with claim 1, wherein a cannula forms the first outlet.

10. The dispensing outlet in accordance with claim 9, wherein the cannula is more flexible than the housing.

11. The dispensing outlet in accordance with claim 9, wherein the cannula is formed from a material different from that of a remainder of the housing.

12. The dispensing outlet in accordance with claim 11, wherein the cannula is formed from metal.

13. The dispensing outlet in accordance with claim 9, wherein the cannula is made from a same material as the housing.

14. The dispensing outlet in accordance with claim 1, wherein a spacing between the pre-determined breaking point and an end of the mixing or reception space that is arranged closest to the pre-determined breaking point is less than an inner diameter of the housing surrounding the mixing or reception space.

15. The dispensing outlet in accordance with claim 1, wherein the pre-determined breaking point is formed in a wall of the housing.

16. The dispensing outlet in accordance with claim 1, wherein the pre-determined breaking point extends peripherally around the housing.

17. The dispensing outlet in accordance with claim 1, wherein the housing has a wall thickness which is larger than a wall thickness of the pre-determined breaking point.

18. The dispensing outlet in accordance with claim 1, wherein the pre-determined breaking point is configured to withstand internal pressures of up to 5 bar before leaking.

19. The dispensing outlet in accordance with claim 1, wherein an internal diameter of the housing at the pre-determined breaking point is smaller than an internal diameter of a part of the housing forming the mixing or reception space, is larger than the internal diameter of that part of the housing forming the mixing or reception space or is the same as the internal diameter of that part of the housing forming the mixing or reception space.

20. The dispensing outlet in accordance with claim 1, wherein the second end comprises a coupling section via which the dispensing outlet is capable of being coupled to a cartridge.

21. The dispensing outlet in accordance with claim 20, wherein the coupling section comprises an inlet section via which multi-component material is capable of being guided to the dispensing outlet.

22. The dispensing outlet in accordance with claim 1, wherein a wall thickness of the housing at a position of the pre-determined breaking point is selected in the range of 0.1 to 0.2 mm.

23. The dispensing outlet in accordance with claim 1, wherein the housing comprises a plastic; an elastomer; or a thermosetting resin.

24. The dispensing outlet in accordance with claim 1, wherein an internal diameter of the housing reduces in size between the pre-determined breaking point and the first outlet.

25. The dispensing outlet in accordance with claim 24, wherein the internal diameter of the housing reduces from a size of 100% at the pre-determined breaking point to a size selected in the range of 1 to 30% of the housing at the first outlet.

26. The dispensing outlet in accordance with claim 1, wherein the pre-determined breaking point is a first pre-determined breaking point and the dispensing outlet further comprises a second pre-determined breaking point arranged between the first pre-determined breaking point and the first outlet, the second pre-determined breaking point forming a third outlet that is arranged at a position of the second pre-determined breaking point and that is set free on separating the first outlet from the housing via the second pre-determined breaking point.

27. The dispensing outlet in accordance with claim 26, wherein the third outlet has a third outlet opening having a diameter larger than the diameter of the first outlet opening, but smaller than the diameter of the second outlet opening.

28. An injection mold configured to form the dispensing outlet in accordance with claim 1, the injection mold comprising:

an internal space configured to resemble an internal and external shape of the housing, with the internal space comprising an internal surface with one or more projections projecting from the internal surface reflecting the shape of the pre-determined breaking point or with one or more shutter elements being moveably formed in the mold with the one or more shutter elements forming projections that project into the injection mold to form the pre-determined breaking point at the housing of the dispensing outlet.

29. A method of making the dispensing outlet in the injection mold in accordance with claim 28, the method comprising:

injecting a molten mass of material into the internal space of the injection mold to integrally form the pre-determined breaking point at the housing of the dispensing outlet.

\* \* \* \* \*